United States Patent
Tsai et al.

(10) Patent No.: US 12,018,055 B2
(45) Date of Patent: Jun. 25, 2024

(54) METHOD FOR PREVENTING HUMAN CELL INFECTION BY HERPESVIRUSES

(71) Applicant: National Yang Ming Chiao Tung University, Taiwan (TW)

(72) Inventors: Ming-Han Tsai, Taipei (TW); Tung-Yi Lin, Taipei (TW)

(73) Assignee: NATIONAL YANG MING CHIAO TUNG UNIVERSITY, Taipei (TW)

( * ) Notice: Subject to any disclaimer, the term of this patent is extended or adjusted under 35 U.S.C. 154(b) by 0 days.

(21) Appl. No.: 18/058,516

(22) Filed: Nov. 23, 2022

(65) Prior Publication Data

US 2024/0166699 A1    May 23, 2024

(51) Int. Cl.
| | | |
|---|---|---|
| *C07K 14/00* | (2006.01) | |
| *A61P 31/20* | (2006.01) | |
| *A61P 35/00* | (2006.01) | |
| *C07K 14/375* | (2006.01) | |

(52) U.S. Cl.
CPC ............ *C07K 14/375* (2013.01); *A61P 31/20* (2018.01); *A61P 35/00* (2018.01)

(58) Field of Classification Search
CPC ......... C07K 14/375; A61P 31/20; A61P 35/00
See application file for complete search history.

(56) References Cited

PUBLICATIONS

Cao et al. Front. Pharmacol., Oct. 25, 2018.*
Darija et al. Antioxidant, antibacterial, antitumor, antifungal, antiviral, anti-inflammatory, and nevroprotective activity of Ganoderma lucidum: An overview. (2022) Front. Pharmacol. 13:934982.*

\* cited by examiner

*Primary Examiner* — Jeanette M Lieb
(74) *Attorney, Agent, or Firm* — HSML P.C.

(57) ABSTRACT

Provided herein is a method for preventing or treating an Epstein-Barr virus (EBV) infection, including administering to the subject in need thereof with an effective amount of immunomodulatory protein of *Ganoderma*, a recombinant thereof, or a fungal immunomodulatory protein of a similar structure. Also provided is a method for preventing or treating an EBV-associated cancer.

8 Claims, 13 Drawing Sheets

Specification includes a Sequence Listing.

METHOD FOR PREVENTING HUMAN CELL INFECTION BY HERPESVIRUSES

BACKGROUND

Technical Field

The present disclosure relates to methods for preventing or treating human epithelial cells and B cells infection by herpesviruses. The disclosure also provides methods for reducing Epstein-Barr virus (EBV) infection of human epithelial cells and B cells. In particular, the methods of the present disclosure relate to administration of an effective amount of an immunomodulatory protein of *Ganoderma* (e.g., *Ganoderma microsporum* immunomodulatory protein (GMI)) to a subject in need thereof, wherein the immunomodulatory protein of *Ganoderma* is in a form of a pharmaceutical composition, a recombinant thereof, or a fungal immunomodulatory protein of a similar structure.

SEQUENCE LISTING

The present application is being filed along with a Sequence Listing in electronic format. The Sequence Listing is provided as a file entitled 211098US-Sequence listing.XML, created on Oct. 17, 2022, which is 4,393 bytes (about 4.29 KB) in size. The information in the electronic format of Sequence Listing is incorporated herein by reference in its entirety.

DESCRIPTION OF RELATED ART

Herpesviruses are members of Herpesviridae which is a large family of DNA viruses. It has been shown that at least 8 herpesvirus types are commonly spread among humans including herpes simplex viruses 1 and 2, varicella-zoster virus, Epstein-Barr virus (EBV), human cytomegalovirus (HCMV), herpesvirus 6, 7, and Kaposi Sarcoma-associated virus (KSHV). Furthermore, EBV is a member of the herpes virus family. EBV is a contagious DNA human gamma herpes virus which could be easily transmitted through different types of body fluids, such as saliva. Generally, EBV initiates a life-long asymptomatic infection in over 95% of the adult population globally. EBV is also well-known for its oncogenic properties and the ability to transform infected host cells. In 21$^{st}$ century, cancer is one of the most notorious diseases without a real cure available. The incidence of cancer even continuously grows among all genders, occupations, and ages. A diverse range of lymphomas and carcinoma malignancies has been recognized as EBV-associated cancers, including Burkitt's lymphoma (BL), Hodgkin's lymphoma (HL), post-transplant lymphoproliferative disease (PTLD), nasopharyngeal carcinoma (NPC), gastric carcinoma, breast cancer, and colorectal cancer. Preventing and treating have drawn a lot of attention nowadays. Every year, 200,000 cancer cases are estimated to be contributed by EBV and around 2% of all cancer mortality is defined as EBV-related. In immune system, B cells, a type of white blood cell, are involved as a humoral immunity component of the adaptive immune system. As a result, B cells produce antibody molecules and contribute to the immune system. *Ganoderma microsporum* immunomodulatory protein, or GMI, is a small fungal protein which is cloned from *G. microsporum*, a species of *Ganoderma* polypore fungi. In East Asian culture, *Ganoderma* has been long used as a traditional Chinese medicine to enhance health and promote longevity.

Unfortunately, due to the complexity of EBV genome, no prophylactic EBV-based cancer vaccine is efficient enough and commercially available. Therefore, in addition to EBV-based vaccination development, the advancement of other strategies using nature products such as GMI to diminish or treat symptoms or infection by herpesviruses is crucial.

SUMMARY

Provided herein is a method for preventing or treating a viral infection, comprising contacting the B cells with an effective amount of an immunomodulatory protein of *Ganoderma*, a recombinant thereof, or a fungal immunomodulatory protein of a similar structure.

In at least one embodiment of the present disclosure, the immunomodulatory protein of *Ganoderma* or the recombinant thereof has:

```
an amino acid sequence of
                                        (SEQ ID NO: 1)
(1) LAWNVK, (SEQ ID NO: 2)
(2) DLGVRPSYAV, (3) an amino acid sequence of
                                        (SEQ ID NO: 3)
MSDTALIFTLAWNVKQLAFDYTPNWGRGRPSSFIDTVTFPTVLTDKAYT

YRVVVSGKDLGVRPSYAVESDGSQKINFLEYNSGYGIADTNTIQVYVID

PDTGNNFIVAQWN;
or an amino acid sequence of
                                        (SEQ ID NO: 4)
EAEAEFMSDTALIFTLAWNVKQLAFDYTPNWGRGRPSSFIDTVTFPTVL

TDKAYTYRVVVSGKDLGVRPSYAVESDGSQKINFLEYNSGYGIADTNTI

QVYVIDPDTGNNFIVAQWNYLEQKLISEEDLNSAVDHHHHHH.
```

In at least one embodiment of the present disclosure, the inhibition of virus infection to a human epithelial cell and a B cell is the induction of interacting of the immunomodulatory protein of *Ganoderma* or the recombinant thereof. In at least one embodiment of the present disclosure, the *Ganoderma* is *Ganoderma lucidum, Ganoderma tsugae, Ganoderma microsporum* or *Ganoderma sinensis*. In at least one embodiment of the present disclosure, the immunomodulatory protein is selected from the group consisting of LZ-8, FIP-gts, GMI, FIP-gja, a recombinant LZ-8, a recombinant FIP-gts, a recombinant GMI and a recombinant FIP-gja.

In at least one embodiment of the present disclosure, the virus is selected from the group consisting of herpes simplex viruses 1 and 2, varicella zoster virus, Epstein-Barr virus (EBV), and human cytomegalovirus (HCMV), herpesvirus 6, 7, and Kaposi Sarcoma-associated virus (KSHV). In at least one embodiment of the present disclosure, the virus is Epstein-Barr virus (EBV).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure can be more fully understood by reading the following descriptions of the embodiments, with reference made to the accompanying drawings.

FIG. 1C shows the survival rate of HEK293 was not affected by the treatment with GMI at various concentrations determined by MTT assay. FIG. 1D illustrates the treatment of GMI reduced EBV infectivity in a dose-dependent manner. FIG. 1E shows that the survival rate of AGS was not affected by GMI at various concentrations determined by MTT assay. $*P<0.5$; $P<0.1$; $*P<0.01$; $****P<0.001$.

FIG. 2C shows the quantification results of FIGS. 2A and 2B. $*P<0.5$; $P<0.1$; $*P<0.01$; $****P<0.001$.

In FIG. 3A, EBV was pretreated with or without GMI before performing infection. Cells were then analyzed by flow cytometry to compare the infectivity rates of the treated and non-treated viruses. The result demonstrates a 50% drop of EBV infectivity in HEK293 cells infected by GMI-pretreated EBV in comparison with HEK293 cells infected by non-pretreated EBV as control, which indicated that GMI indeed targeted the virus during this process. FIG. 3B shows the GMI-pretreated HEK293 cells (for 24 hours or 48 hours) were infected by EBV together with or without GMI treatment during infection period. The results show that 24- and 48-hour pre-treatment of HEK293 only before infection could reduce the portion of GFP-positive cells by half whereas the treatment of before together with during infection could assure nearly zero infectivity. In FIG. 3C, FACS analysis of GFP-positive cells proved that infectivity decreased at 2, 6, 12, 24, and 48 hours indicating the effect of GMI was transient. $*P<0.5$; $P<0.1$; $*P<0.01$; $****P<0.001$.

DETAILED DESCRIPTION OF THE EMBODIMENTS

Figure 1A:
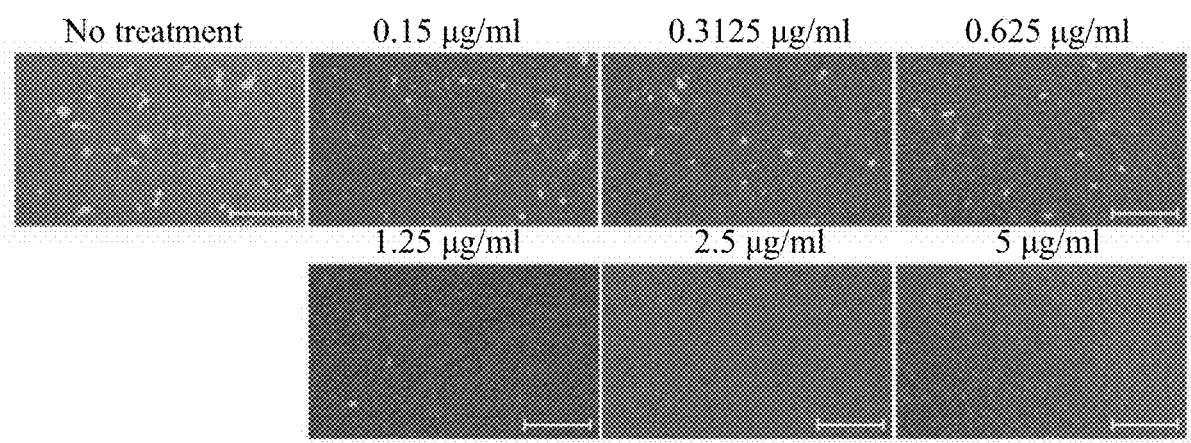
FIGS. 1A to 1C illustrate the treatment with GMI at different concentrations decreased the infectivity rate of recombinant M81 EBV strain expressing GFP in HEK293 cells. GMI inhibited the infection of recombinant M81 EBV strain expressing GFP in HEK293 in a dose-dependent manner determined by a fluorescence microscopy (FIG. 1A) and flow cytometry (FIG. 1B).

The technical solutions illustrated in the examples of the present disclosure will now be described more clearly and completely, and it will be apparent that the described examples are merely part of the examples of the present disclosure and are not intended to be exhaustive. The present disclosure can also be implemented or applied as described in different examples. A person skilled in the art can easily conceive the other advantages and effects of the present disclosure, based on the disclosure of the specification. It is possible to modify or alter the above examples for carrying out this disclosure without contravening its scope, for different aspects and applications.

Generally, all technical and scientific terms used herein generally have the same meaning as commonly understood by one of ordinary skill in the art to which this disclosure belongs. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the descriptions of the present disclosure. Thus, the terms used herein have to be defined based on the meaning of the terms together with the descriptions throughout the specification.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, which are included in the present disclosure, yet open to the inclusion of unspecified elements or steps, whether essential or not.

Also, when a part "includes" or "comprises" a component or a step, unless there is a particular description contrary thereto, the part can further include other components or other steps, not excluding the others.

The terms "subject," "patient" and "individual" are used interchangeably herein and refer to a warm-blooded animal including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In some embodiments, the subject is a human.

According to the disclosure, the terms "treat," "treatment," "treating" and the like are used herein to generally mean obtaining a desired pharmacologic or physiologic effect. The effect may be prophylactic in terms of completely or partially preventing a condition, appearance, disease or symptom and/or may be therapeutic in terms of a partial or complete cure for a condition and/or adverse effect attributable to a condition or disease. The term "treatment" as used herein covers any treatment of a condition, disease or undesirable appearance in a mammal, e.g., a human, and includes: (a) preventing the disease (e.g., cancer), condition (pain) or appearance (e.g., visible tumors) from occurring in a subject which may be predisposed to it but has not yet been observed or diagnosed as having it; (b) inhibiting the disease, condition or symptom, i.e., causing regression of a condition or symptom; and (c) relieving the disease, condition or symptom, i.e., causing regression of a condition or symptom.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, the term "recombinant" may refer to the alteration of genetic material by human intervention. For example, recombinant may refer to the manipulation of DNA or RNA in a cell or virus or an expression vector by molecular biology (recombinant DNA technology) methods, including cloning and recombination. Recombinant may also refer to manipulation of DNA or RNA in a cell or virus by random or directed mutagenesis. A "recombinant" nucleic acid can be described with reference to how it differs from a naturally occurring counterpart (the "wild-type"). A recombinant protein may refer to a protein expressed by recombinant DNA technology. A recombinant protein has a similar amino acid sequence and maintains the same activity or function as its parental protein.

The term "contacting" or "contact" is meant to refer to bringing together of a cosmetic or therapeutic agent and cell or tissue such that a physiological and/or chemical effect takes place as a result of such contact. Contacting can take place in vitro, ex vivo, or in vivo. In some embodiments, a cosmetic or therapeutic agent is in contact with a cell in a cell culture (in vitro) to determine the effect of the cosmetic or therapeutic agent on the cell. In some embodiments, the contacting of a cosmetic or therapeutic agent with a cell or tissue includes the administration of a cosmetic or therapeutic agent to a subject having the cell or tissue to be contacted.

As used herein, the term "virus" refers to a type of microorganism that can include both pathogenic and non-pathogenic viruses. Pathogenic viruses can be classified into two general types with respect to the viral structure: enveloped viruses and non-enveloped viruses. Some well-known enveloped viruses include herpes virus, influenza virus; paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus. It is known in the art that "enveloped" viruses are relatively sensitive and, thus, can be inactivated by commonly used disinfectants. In contrast, non-enveloped viruses are substantially more resistant to conventional disinfectants and are significantly more environmentally stable than enveloped viruses.

Lingzhi, an herbal mushroom, used in traditional Chinese medicine for at least 2,000 years, is a species complex that encompasses several fungal species of the genus $Ganoderma$, most commonly $Ganoderma\ lucidum,\ Ganoderma\ tsugae$, and $Ganoderma\ sichuanense$, which are closely related. Many therapeutic effects have been reported of Lingzhi, such as immunomodulatory, anti-tumor, hepatoprotective, antioxidant, and cholesterol-lowering effects (Jinn et al., 2006, Biosci. Biotechnol. Biochem., 70, 2627-2634). Most of these therapeutic effects are attributed to triterpenoids, polysaccharides, and glycoproteins (Boh et al., 2007, Biotechnol. Annu. Rev., 13, 265-301; Jinn et al., 2006, Biosci. Biotechnol. Biochem., 70, 2627-2634). A glycoprotein class in Lingzhi named fungal immunomodulatory proteins (FIPs) has recently been identified. So far, at least 5 FIPs have been isolated, i.e., LZ-8, ($Ganoderma\ lucidum$), FIP-gts ($Ganoderma\ tsugae$), FIP-gja ($Ganoderma\ sinensis$) and GMI ($Ganoderma\ microsporum$) (Ko et al., 1995, Eur. J. Biochem., 228, 244-249).

The present disclosure relates to an immunomodulatory protein of $Ganoderma\ microsporum$ (GMI) that is effective in suppressing infection by EBV. For example, the GMI induces PD-L1 degradation in a cancer cell through the proteasomal degradation system. The GMI activates GSK3f3, thereby inducing PD-L1 degradation in a cancer cell. The PD-L1 expression in a lung cancer-bearing mouse is downregulated by GMI. In addition, the combination of GMI and anti-PD-1 antibody suppresses tumor growth in the lung cancer-bearing mouse. These findings suggest GMI's efficacy in cancer immunotherapy.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The terms "active ingredient" and "active substance" refer to a compound, which is administered, alone or in combination with one or more cosmetically or pharmaceutically acceptable excipients, to a subject for preventing, ameliorating or treating one or more symptoms of a disorder, disease, or condition. As used herein, "active ingredient" and "active substance" may be an optically active isomer of a compound described herein.

The terms "drug," "cosmetic agent" and "therapeutic agent" refer to a compound or a cosmetically or pharmaceutical composition thereof, which is administered to a subject for preventing, ameliorating or treating one or more symptoms of a disorder, disease, or condition.

In one aspect, the method of the present disclosure for treating cancer comprises suppression of tumor growth, progression, or recurrence. In another aspect, the method of the present disclosure for treating cancer comprises prevention of cancer development.

In one embodiment, the $Ganoderma$ immunomodulatory protein, a recombinant thereof, or a fungal immunomodulatory protein of a similar structure is derived from $Ganoderma\ lucidum,\ Ganoderma\ tsugae,\ Ganoderma\ microsporum$ or $Ganoderma\ sinensis$. For example, the immunomodulatory protein is LZ-8 derived from $Ganoderma\ lucidum$, FIP-gts derived from $Ganoderma\ tsugae$, GMI derived from $Ganoderma\ microsporum$, or FIP-gja derived from $Ganoderma\ sinensis$ or a recombinant thereof. In some embodiments, the immunomodulatory protein is derived from $Ganoderma\ microsporum$ (GMI) or $Ganoderma\ lucidum$ (LZ-8).

Materials and Methods

Ethics Statement

All human primary B cells utilized in this study were isolated from healthy donors with informed consent documented.

GMI

GMI was provided by MycoMagic Biotechnology Co., Ltd. (New Taipei, Taiwan). Different concentrations of GMI were used and specified in each experiment.

Cell Lines and Primary Cells Culture

Cell lines used in this study: HEK293 human embryonic kidney cells (ATCC CRL-1573), AGS human gastric adenocarcinoma cells (ATCC CRL-1739) and all the lymphoma cell lines (kindly provided by Prof. Henri-Jacques Delecluse). Cells were routinely maintained in RPMI-1640 medium (Gibco) supplemented with 10% fetal bovine serum (FBS, HyClone) in a humidified cell culture incubator at 37° C. under 5% $CO_2$. Ficoll-Paque Plus was added to diluted whole blood to separate peripheral blood mononuclear cells (PBMCs) and primary B cells isolation from PBMCs was conducted using Dynabeads CD19 Pan B (Invitrogen) and DETACHaBEAD CD19 kit (Invitrogen). Lymphoblastoid cell lines (LCLs) were generated from primary B cells infection with EBV strain M81. Primary B cells culture medium was supplemented with 20% FBS during EBV infection and until they were transformed to LCLs.

Transfection

PEI MAX (MW 40,000, Polysciences 24765-1) was applied to perform all transfection experiments complying with manufacturer's instructions for use.

Epithelial Cell Viability Assay $5 \times 10^3$ AGS cells per well were cultured in 96-well plate in 12 hours. Different concentrations of GMI were then added into cells culture medium for 24-48 hours. Cells viability was finally evaluated by MTT assay.

Lymphoma Cells and LCLs Viability Assay $10^4$ cells/well of each inspected lymphoma cells and LCLs were seeded into 96-well plate with different GMI dilutions. After 24-48 hours of treatment, cells viability was examined by flow cytometry (FACSCalibur).

Recombinant EBV (rEBV) and Stable Virus-Producing Cells

M81 was cloned onto an F-plasmid in order to express GFP as previously described. Stable virus-producing 293 cells were generated using the recombinant EBV-BAC similarly to a 2015 study.

Virus Production

Stable EBV-producing HEK293 cells were co-transfected with plasmids expressing BZLF1 (p509) and gp110 (pRA). 24 hours post transfection, culture medium was refreshed with RPMI-1640 supplemented with 10% FBS. Virus supernatant was collected after another 84 hours and was then filtered through a 0.45 μm filter. Virus supernatant used for EBV infection was concentrated by high-speed centrifugation (22,000×g for 2 hours at 4° C.) and resuspended in RPMI-1640 with 10% of FBS.

Quantitative Real-Time PCR (qPCR)

Quantification of EBV copies per milliliter of virus supernatant was carried out by qPCR. The examined supernatant was first treated with DNaseI (0.1 ug/ul) and proteinase K (5 mg/ml) before being subjected for qPCR with primers and probe against EBV BALES gene. To quantify the number of EBV copies per cell for binding assay, extracted genomic DNA of cells sample was analyzed by qPCR targeting EBV and actin simultaneously. Actin was used as a control to normalize the amount of cells subjected in each sample.

Epithelial Cells Infection

For HEK293 infection, 2500 cells per well were incubated in 96-well plate for 12 hours before GMI treatment at different concentrations and conditions as indicated in each experiment. After specific treatment time, culture medium was removed and fresh medium containing rEBV with or without GMI was added according to experiments design. 48 hours post infection, culture medium was replenished again and cells were incubated to recover for another 2 days prior to fluorescence microscopy (Zeiss) analysis. Finally, the cells survival rate and the infectivity rate of EBV were evaluated by the percentage of alive cells and GFP-positive HEK293 cells through flow cytometry (FACSCalibur). In terms of transfer infection on AGS, firstly isolated primary B cells were exposed to EBV at a multiplicity of infection (MOI) of 100 viral genomes per cell for 2 hours at 4° C. and unbound viruses were washed off thereafter. These B cells were incubated in RPMI-1640 with 20% FBS in 20 hours and were cocultured with AGS in 8-well chamber slide in 48 hours with/without GMI treatment. Careful removal of B cells was conducted with PBS, following by cells recovery in one day. Finally, the infected AGS cells were quantified by EBER ISH along with cytokeratin immunofluorescence staining and nuclei counterstaining with Hoechst 33342.

B Cells Infection

EBV was used to infect CD19+ isolated human B cells at a 50 MOI in 2 hours at 4° C. on a rolling device before all unbound viruses were washed off by centrifugation. The B cells were then cultured in U-bottom 96-well plate with RPMI-1640 20% FBS for 72 days. The percentage of infected B cells was determined by the proportion of EBNA2-positive cells through immunofluorescence staining.

Binding Assay

Virus supernatant was treated with DNaseI (0.1 ug/ul) for 1 hour at 37° C. to cleave free viral DNA. After 1 hour of incubation, EDTA was then added to the viral supernatant to the final concentration of 20 mM to inactivate DNaseI. Treated-virus was exposed to primary B cells (MOI 25) or HEK293 (MOI 200) or AGS (MOI 400). The binding process was performed on a rolling appliance for 2 hours at 4° C., and the cells were washed carefully for 3 times with ice-cold medium. The amount of EBV bound on the host cells were then observed by immunofluorescence staining for EBV gp350 or were detected by extracting DNA from the EBV-bound cell pellets and performing qPCR to quantify EBV copies per cell.

Immunoprecipitation Assay

EBV was treated with GMI (5 ug/ml) or PBS at 4° C. or 37° C. for 2 hours. Samples with or without the removal of supernatant containing GMI were then subjected to immunoprecipitation with Dynabeads Protein G Immunoprecipitation kit (Invitrogen #10007D) according to the manufacturer's instructions. The precipitated samples were then subjected to qPCR to detected EBV copies/ml.

Antibodies

Immunofluorescence staining was performed using mouse monoclonal antibodies against EBNA2 (clone PE2), BZLF1 (clone BZ1, Santa Cruz Biotechnology), gp350 (clone 72A1), cytokeratin pan (Cytokeratin Pan Antibody Cocktail, Invitrogen) and Cyanine3 goat-anti-mouse secondary antibody (Invitrogen).

Immunofluorescence Staining

The cells were smeared onto a glass slide and were fixed for 20 minutes at room temperature with 4% paraformaldehyde in PBS. For EBNA2 and BZLF1 staining, fixed cells were then further permeabilized in PBS 0.5% Triton X-100 for 2 minutes Incubation with first antibody was carried out at 37° C. in 30 min and was followed by 3 washes with PBS before incubation with Cyanine3 second antibody in the similar condition. The cells were washed again in PBS for 3 times prior to mounting with 90% glycerol.

EBER In Situ Hybridization (ISH)

EBER ISH was conducted to inspect the number of AGS infected cells with EBER PNA probe and PNA ISH Detection Kit provided by Dako according to manufacturer's instructions.

Statistical Analysis

Statistical data was analyzed by GraphPad Prism 9. Each experiment was repeated at least 3 times or as indicated, data were presented as mean±SD, and t-test was used to assess the statistical differences. P-value was set as below: *P<0.5; P<0.1; *P<0.01; ****P<0.001.

EXAMPLES

The immunomodulatory protein derived from *Ganoderma microsporum* (hereinafter referred to as "GMI") used in the examples was manufactured by Mycomagic Biotechnology Co., Ltd., according to the method described in U.S. Pat. No. 7,601,808 and has an amino acid sequence of (SEQ ID NO: 3)
MSDTALIFTLAWNVKQLAFDYTPNWGRGRPSSFIDTVTFPTVLTDKAYT

YRVVVSGKDLGVRPSYAVESDGSQKINFLEYNSGYGIADTNTIQVYVID

PDTGNNFIVAQWN.

Example 1: GMI could Substantially Inhibit EBV Infection on Epithelial Cells

Figure 1B:
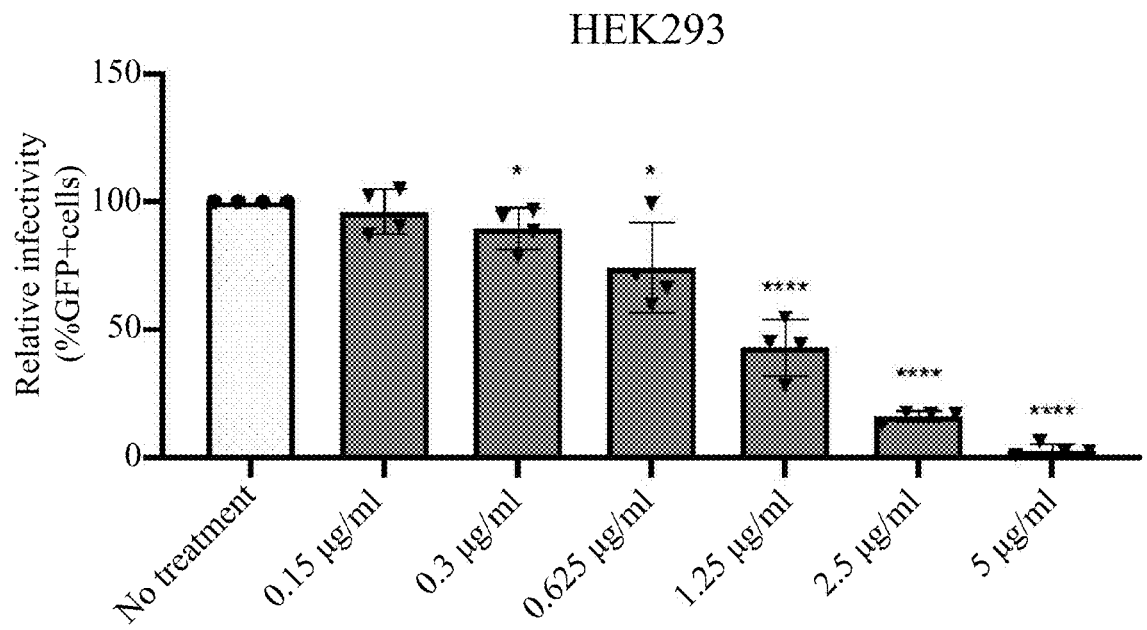
Figure 1C:
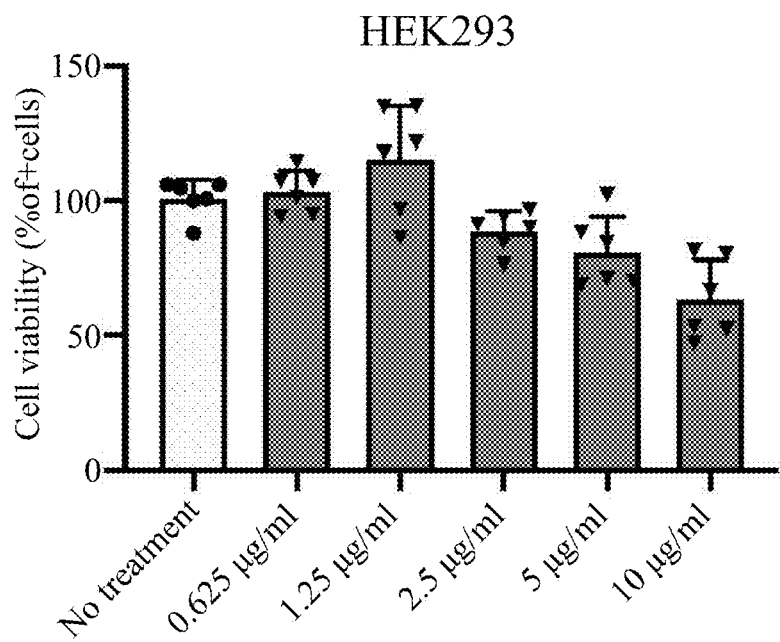
Figure 1D:
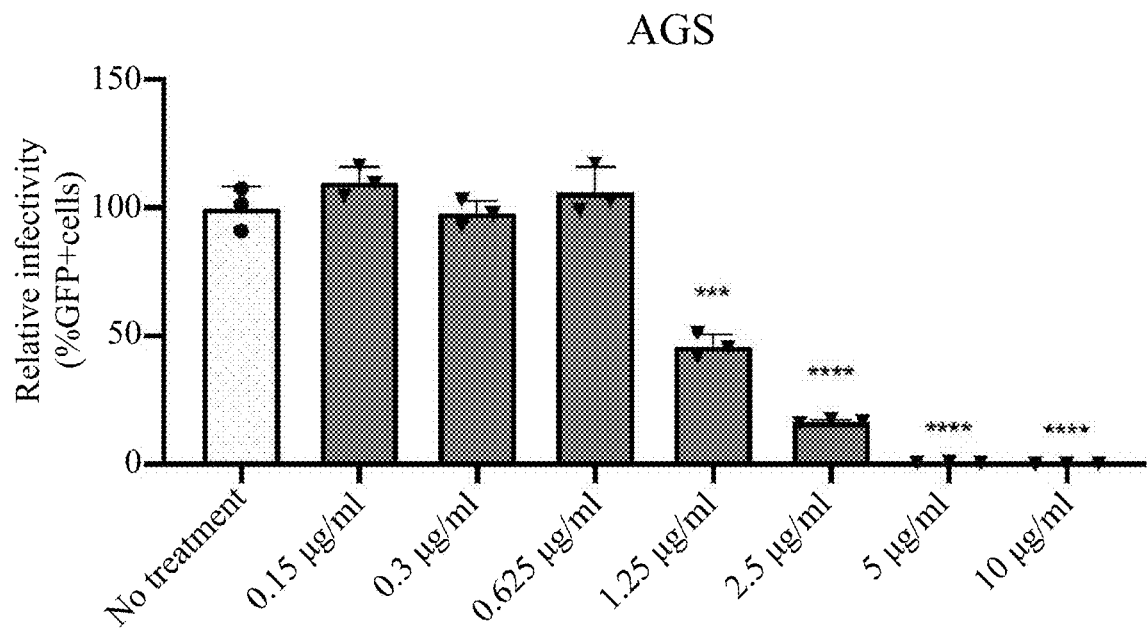
FIGS. 1D and 1E show the effects of GMI against EBV infection in a human gastric adenocarcinoma cell-line (AGS) cells. AGS cells were infected with EBV using transfer infection for 48 hours under different GMI concentrations.
Figure 1E:
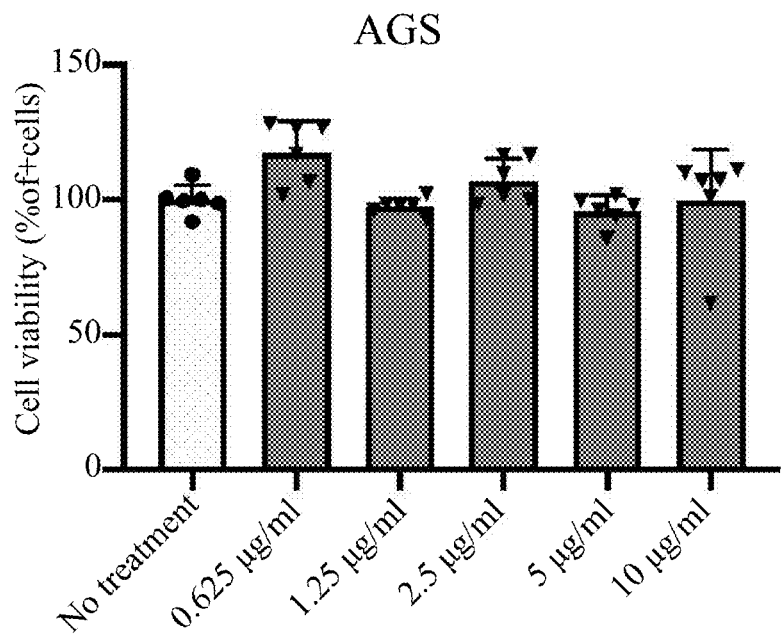

Since EBV is highly attributable to various tumors of epithelial origin, EBV infection on such cells should be thoroughly inspected. In order to have full insights in GMI's ability on manipulating EBV infection of epithelial cells, we chose two different cell lines to perform epithelial infection. Recombinant M81 EBV strain expressing GFP was used to infect HEK293 cells and different concentrations of GMI were added during the 2-day infection period. One sample without any GMI treatment was served as a control. Cells were then analyzed under fluorescence microscopy for GFP signals representing HEK293 infected cells as seen in FIG. 1A. In FIG. 1B, results were further validated by subjecting the samples to flow cytometry. The outcomes were similar in both assays: GMI could reduce EBV infection in HEK293 in a dose-dependent manner and higher concentrations could deliver even more significant efficacy. From 5 μg/ml, EBV barely infected HEK293 anymore. Cell toxicity of GMI was also evaluated by MTT assay to make sure the used concentrations of GMI do not affect cell viability compared to no treatment control as shown in FIG. 1C. Similarly, GMI could also reduce EBV infection on AGS cells (shown in FIG. 1D) at dose-dependent manner without the observation of cytotoxicity (shown in FIG. 1E).

Example 2: GMI could Compromise EBV Infection on Primary B Cells

Figure 2A:
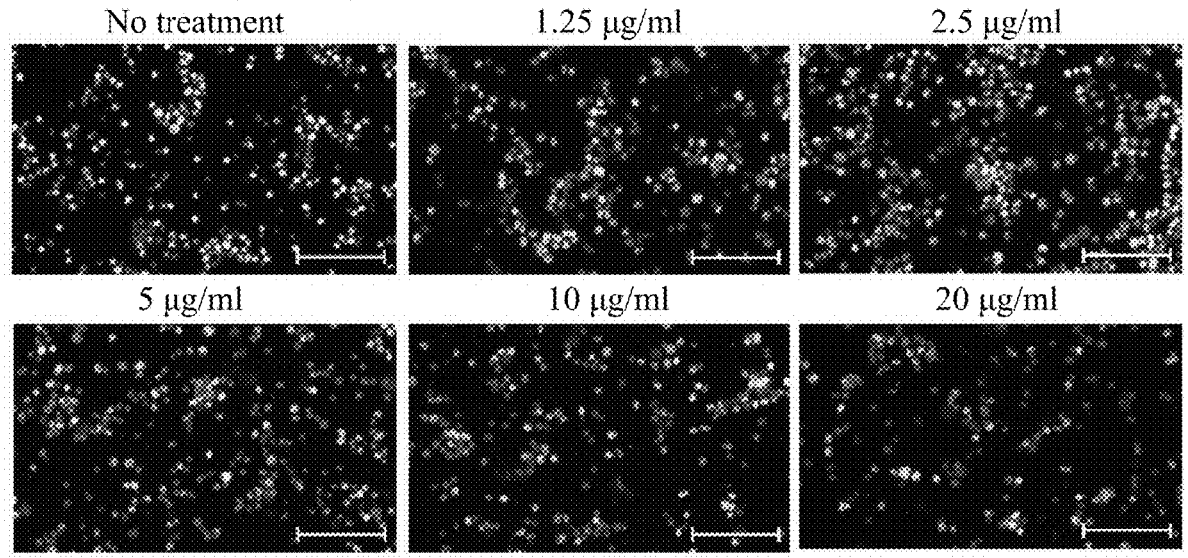
FIGS. 2A to 2C indicate the effects of GMI on primary B cells under different conditions. The infectivity rate in primary B cells was determined by EBNA2-positive B cells observed by immunofluorescence staining. Regardless adding GMI during virus-cells only at viral binding step at 4° C. for 2 hours (FIG. 2A) or with GMI during the 3-day infection period (FIG. 2B), treatment with GMI reduced EBV infectivity rate in a dose-dependent manner and could decrease up to by two-thirds compared to no treatment control.
Figure 2B:
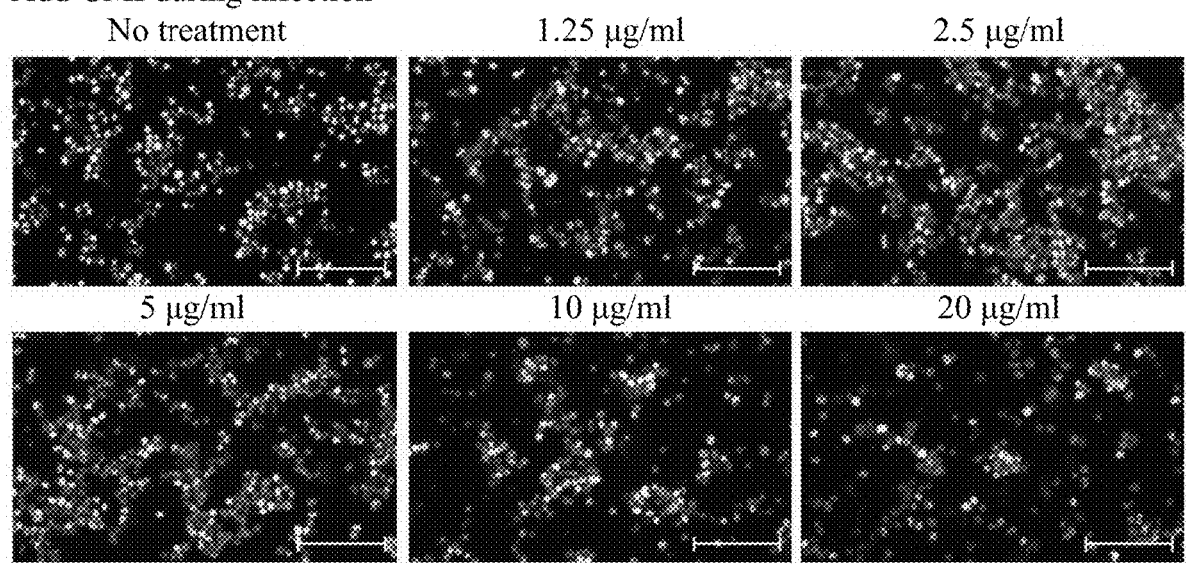
Figure 2C:
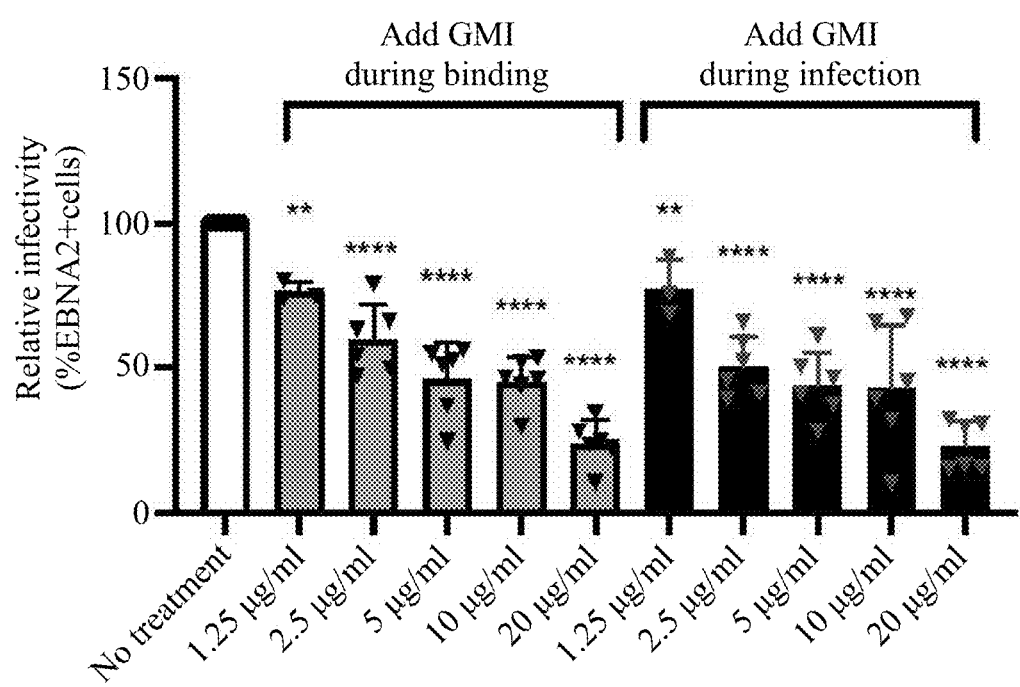

As B cells are one of the main host cells of EBV in human, the impacts of GMI treatment on B cell infection must be concerned. Primary B cells were isolated from whole blood of healthy donors with the help of Ficoll and CD19 Dynabeads. Exposure of EBV to these cells was proceeded in 2 hours at 4° C. (for virus-cell binding), after that all unbound viruses were removed and the samples were cultured for 3 days (for viral infection). Two different treatment conditions were applied in this experiment: GMI of different dilutions were added either during 4° C. virus-cells binding step (shown in FIG. 2A) or during the 3-day infection period (shown in FIG. 2B). EBV infectivity rate was determined by EBNA2 immunofluorescence staining (in percentage; shown in yellow color. The nuclei of all cells were stained with Hoechst 33342 (shown in blue color)) and the final calculated data demonstrated that GMI indeed reduced EBV infectivity on primary B cells. In general, treatment given during binding or during infection period had similar inhibition effects: the higher drug concentration used, the greater effects delivered; from 5 and 10 μg/ml, GMI could decrease infection rate by more than half (compared to no treatment) (shown in FIG. 2C).

Figure 3A:
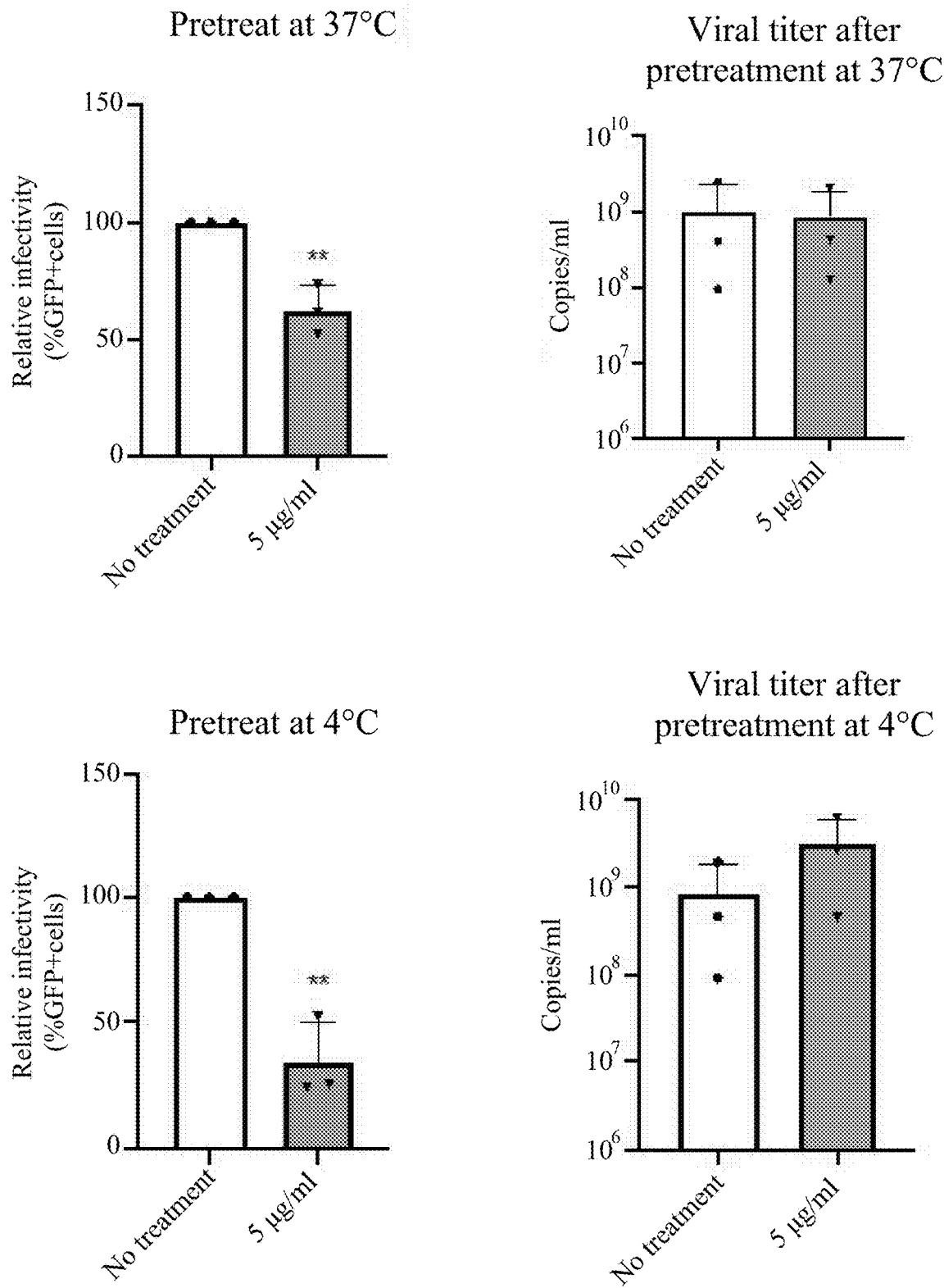
FIGS. 3A to 3C show the inhibitory effects of GMI on EBV infection by targeting both EBV viral particles and the host cells.

Example 3: GMI Inhibits EBV Infection by Targeting Both EBV Viral Particles and Host Cells As GMI was shown to have great inhibition on EBV infection of its main host cells in humans, we wanted to carry out further investigation to specify if the protein targets the virus or the cells to provoke the effect. Firstly, we pretreated the virus with PBS (as a control) or with GMI at 5 μg/ml for 2 hours at either 4° C. or 37° C. before the treated virus was centrifuged at 22,000×g for 2 hours to remove all the PBS/GMI in the supernatant. Subsequently, these viruses were quantified by qPCR for viral titer (copies/ml) and an equal amount of virus was used to infect HEK293 cells in 48 hours. Cells were then analyzed by flow cytometry to compare EBV infectivity of the non-treated and treated virus. The about 50-70% drop in GFP+ cells percentage of treated samples compared to the controls indicated that GMI indeed targeted the virus during this process as shown in FIG. 3A.

Figure 3B:
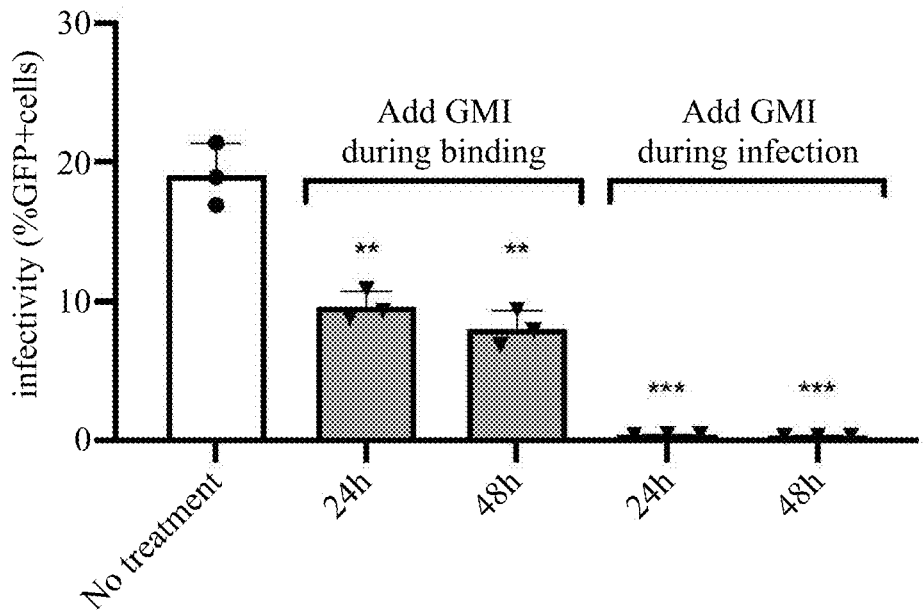
Figure 3C:
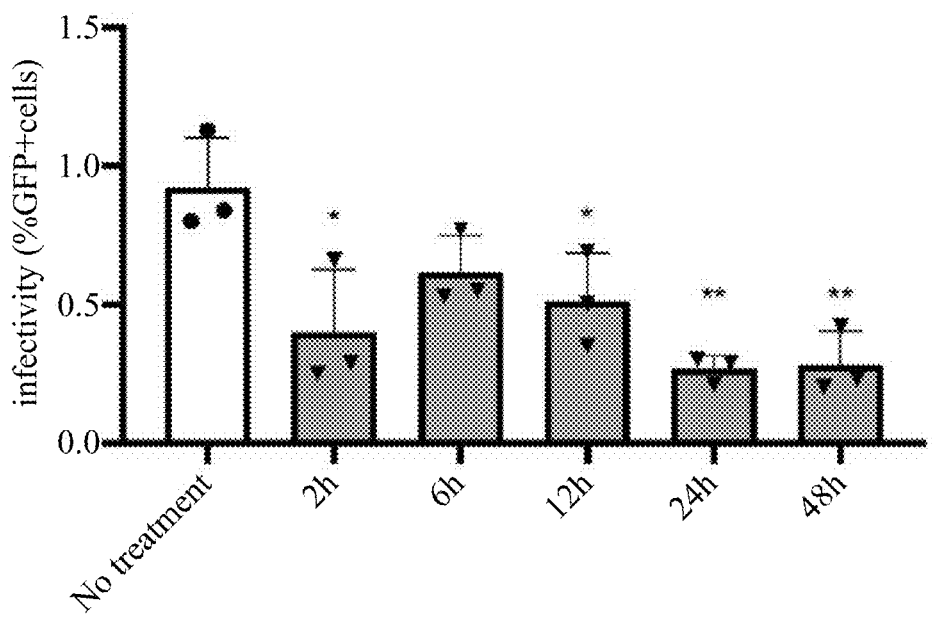
Figure 4A:
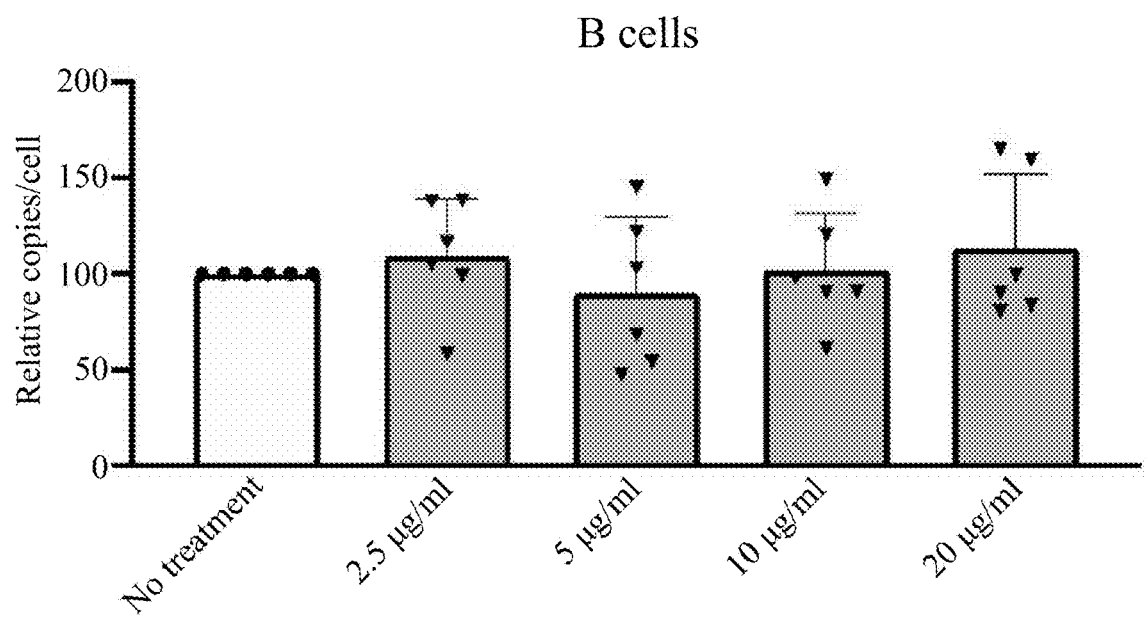
FIGS. 4A to 4E reveal the effects of GMI on EBV binding to the host cells. Overall, GMI showed no significant effects on virus binding to primary human B cells, HEK293 and AGS cells. $*P<0.5$; $P<0.1$; $*P<0.01$; $****P<0.001$.
Figure 4B:
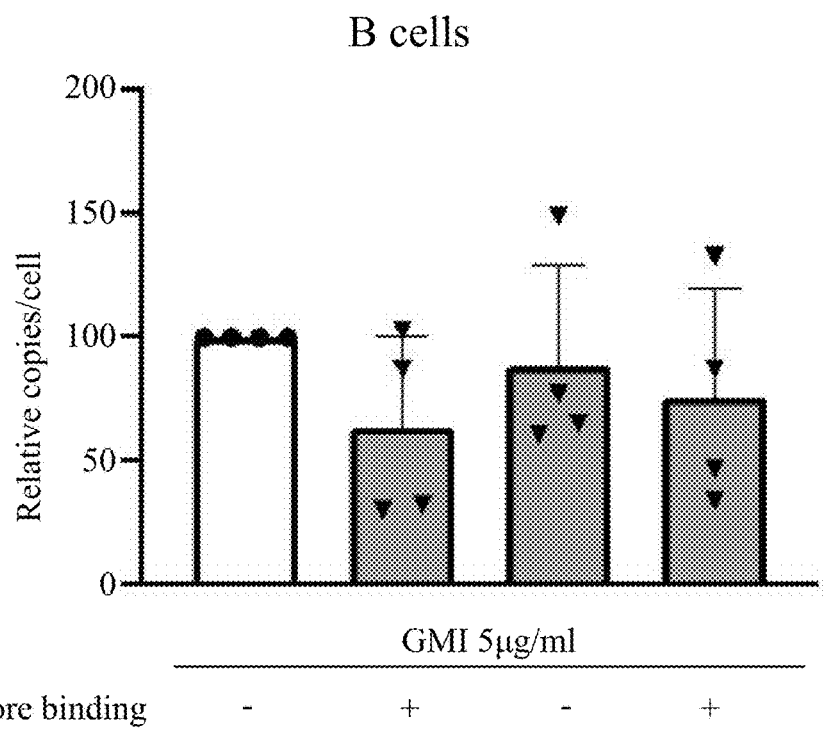
Figure 4C:
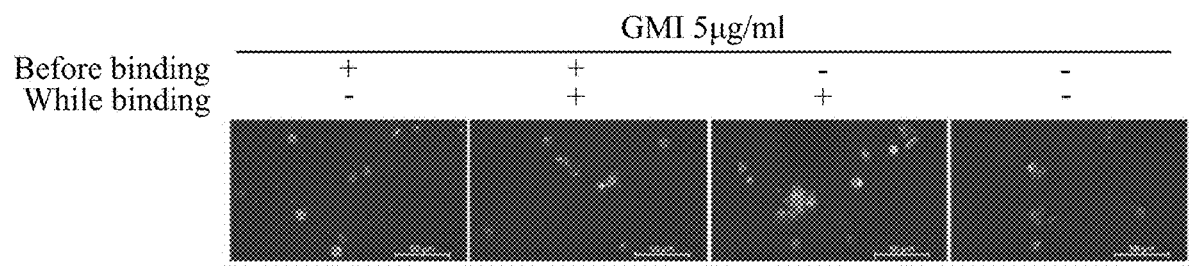
Figure 4D:
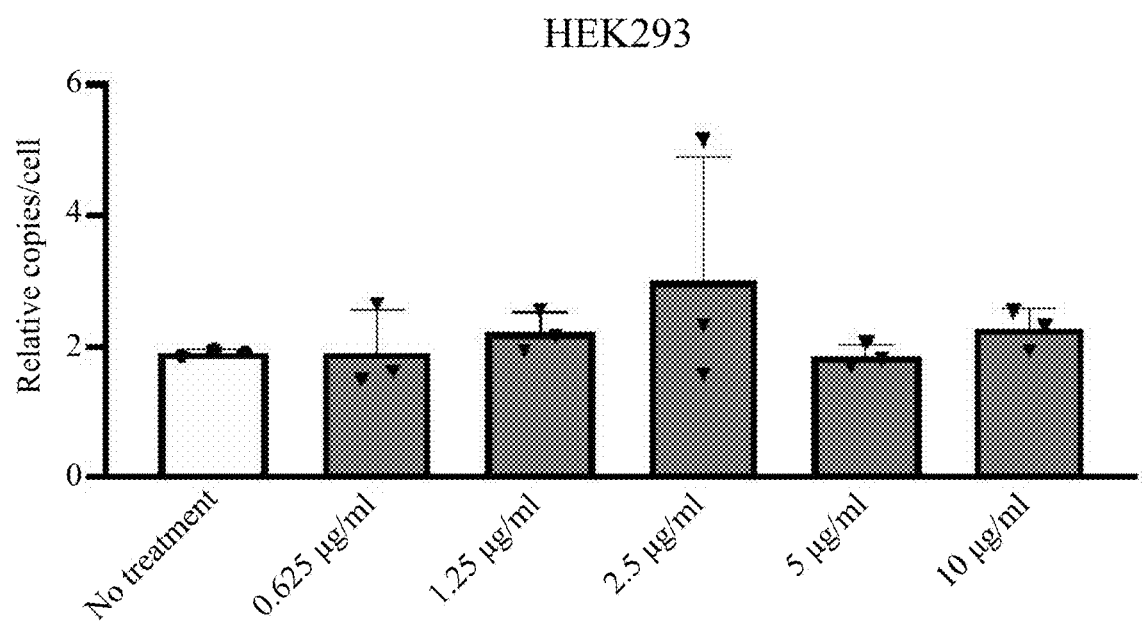
Figure 4E:
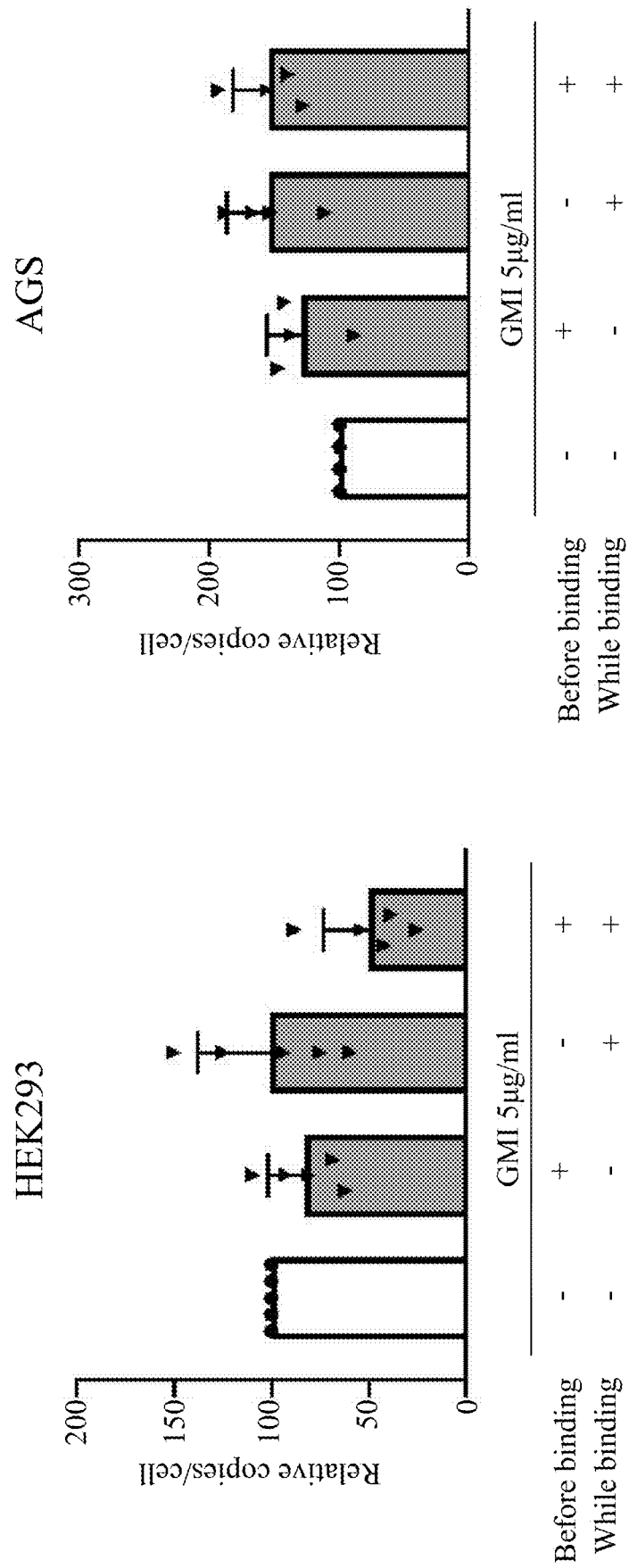

Next, we treated HEK293 for 24 or 48 hours with 5 μg/ml GMI and then removed all the medium and the drug. In FIG. 3B, the treated cells were infected with EBV with or without adding GMI with the same dilution during infection. 24- and 48-hour pretreatment of HEK293 only before infection could reduce the portion of GFP positive cells by half whereas treatment before together with during infection could assure nearly zero infectivity. This finding implied that GMI did target the cells during pretreatment that could also have protection effects against EBV infection later on. The infection time to 12 hours in the next experiment where HEK293 cells were pretreated with 5 μg/ml GMI for 2, 6, 12, 24 and 48 hours before EBV was added. FACS analysis of GFP-positive cells proved that pretreatment for only 2 hours could already trigger the effects (seen in FIG. 3C). Looking specifically at 24- and 48-hour pretreated samples, we found that the lessened infection period (FIG. 3C) gained greater inhibition (approximately 60%) compared to 50% reduction of the previous 2-day infection experiment (shown in FIG. 3B).

Example 4: GMI Did not Affect Virus-Cell Binding

Since GMI has proven itself to have a significant capability on both the virus and the cells, we wanted to further investigate if GMI could alter the binding of EBV and its hosts. In this experiment, virus supernatant was treated with DNaseI at 37° C. to cleave free viral DNA. The treated virus was exposed to HEK293 at a MOI of 200 while the MOI to B cells was 25. Different concentrations of GMI were added during the binding process, which was performed on a rolling appliance for 2 hours at 4° C. before EDTA was added to inactivate DNaseI. All samples were washed carefully 3 times with ice-cold medium. Cells were stained with 72A1 antibody for gp350 expression and genomic DNA extracted from these samples was subjected to qPCR to compare the quantity of EBV copies per cell. The data obtained clarified that at the studied dilutions, GMI had no considerable effects on the binding between EBV and both cells (B cells and HEK293).

Next, we modified GMI treatment conditions to further confirm if the protein could change the virus-cell binding ability or not. In this assay, B cells/HEK293/AGS were pre-treated with GMI for 2 hours at 4° C. (B cells) or 37° C. (HEK293/AGS) (before binding) or during the binding step or at both steps. The same procedures were then performed for immunofluorescence staining and qPCR. Overall, the results showed that GMI has no significant effects in viral binding to the host cells (shown in FIGS. 4A to 4E).

Example 5: GMI Did not Influence Lytic Proteins Expression

Figure 5A:
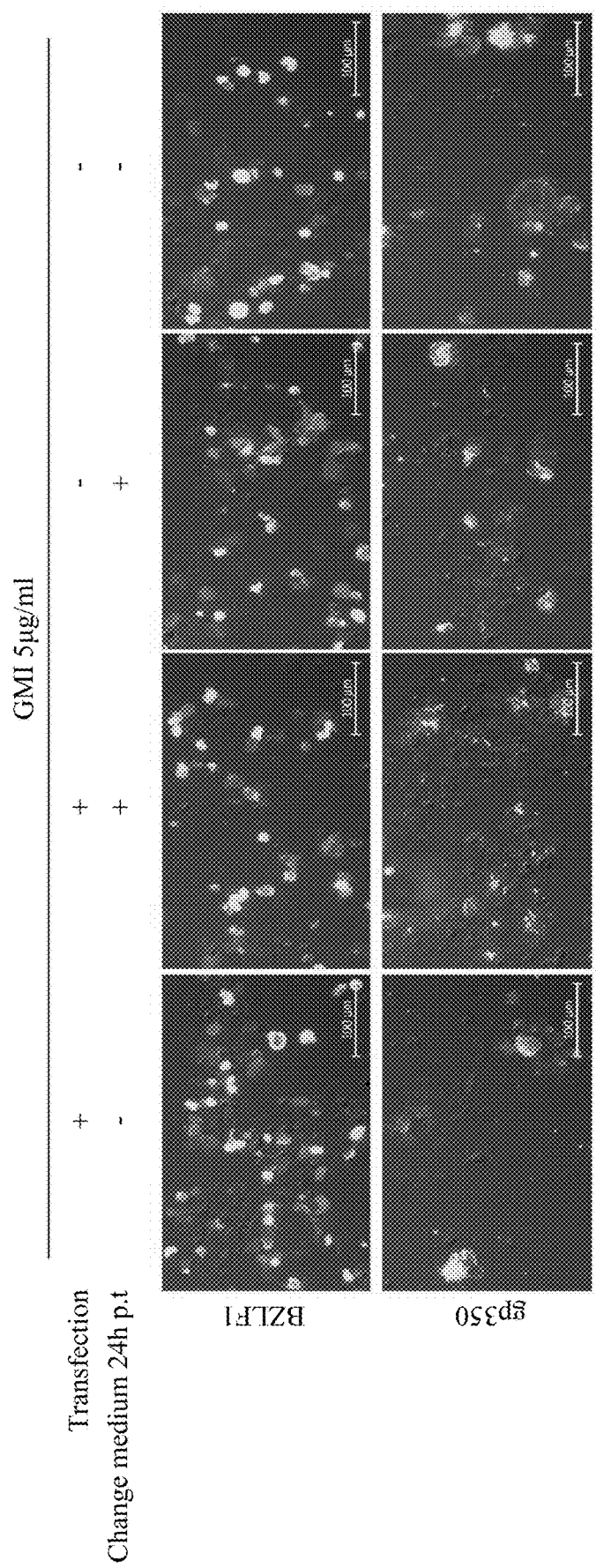
FIGS. 5A and 5B indicate the impacts of GMI on lytic proteins expression in virus producing HEK293 cells and EBV-transformed lymphoblastoid cell lines. No major difference was observed. $*P<0.5$; $P<0.1$; $*P<0.01$; $****P<0.001$.
Figure 5B:
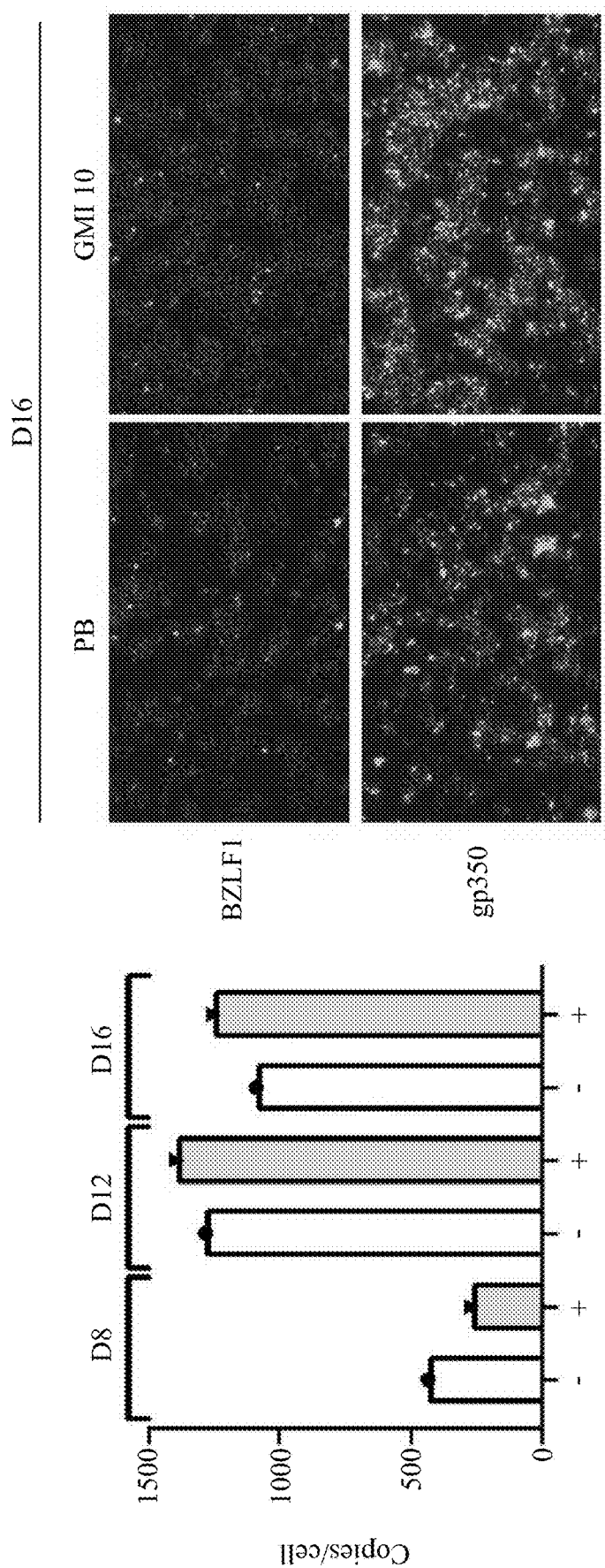

We observed the impacts of GMI on lytic protein expressions on virus-producing HEK293 cells and EBV-transformed lymphoblastoid cell lines by immunofluorescence staining (shown in FIGS. 5A and 5B). As a results, no significant difference was observed.

Example 6: GMI could Interact with EBV

Figure 6A:
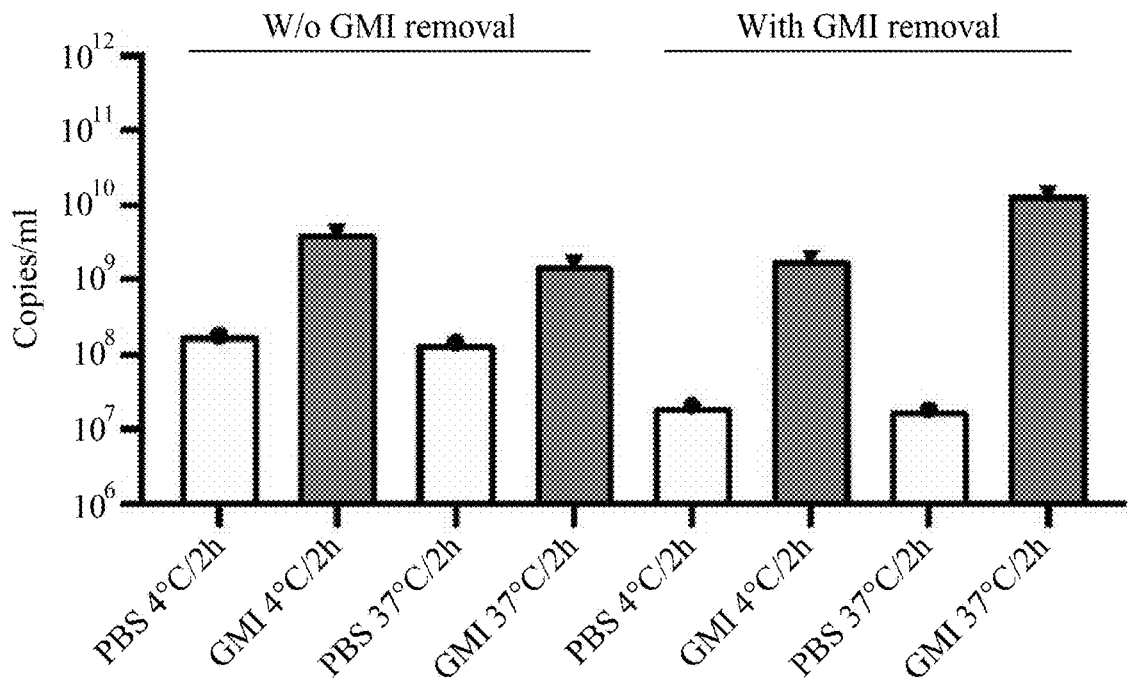
FIGS. 6A and 6B show the interaction between GMI and EBV Viruses were treated with GMI at 5 ug/ml (or with PBS as a control) at 4° C. or 37° C. for 2 hours. Samples with or without the removal of supernatants containing GMI were all then subjected to immunoprecipitation assay. The results showed that EBV could be pulled down with GMI and detected by qPCR thereafter (FIG. 6A), which indicated the interaction between GMI and EBV. qPCR was performed to titrate the virus input used in the immunoprecipitation experiments of FIG. 6B. $*P<0.5$; $P<0.1$; $*P<0.01$; $****P<0.001$.
Figure 6B:
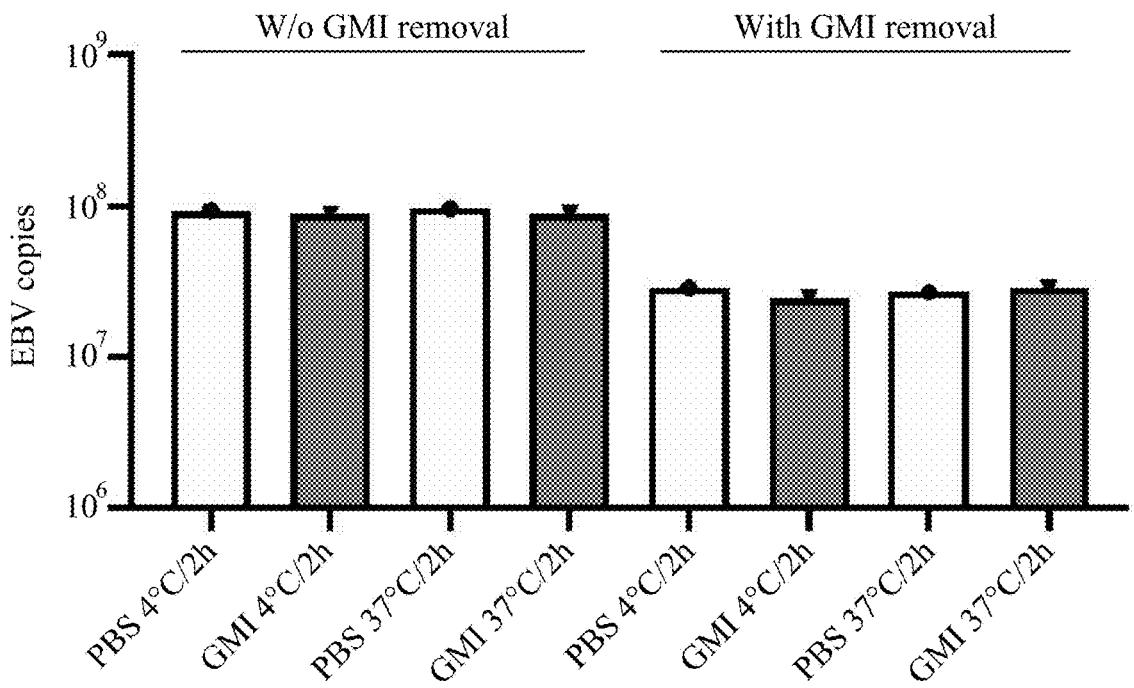

Regarding the significant reduction of EBV infectivity using GMI-pretreated virus, we wanted to examine if the protein has the ability to interact with the viruses. After being treated with GMI at 5 µg/ml (or with PBS as a control) at 4° C. or 37° C. for 2 hours, the viruses were pulled down by immunoprecipitation assay prior to EBV copies/ml quantification with qPCR (seen in FIG. 6A). In one set of samples, GMI was removed (with GMI removal) by centrifugation after treatment (FIG. 6A). Analyzed data showed that GMI could substantially bind to the virus in all repeats at both conditions compared to the PBS controls. FIG. 6B shows the viral titer of the samples used in FIG. 6A.

---

---

What is claimed is:

1. A method for preventing or treating a viral infection, comprising administering to a subject in need thereof an effective amount of an immunomodulatory protein of *Ganoderma* or a recombinant thereof, wherein the immunomodulatory protein is selected from the group consisting of LZ-8, FIP-gts, GMI, FIP-gja, a recombinant LZ-8, a recombinant FIP-gts, a recombinant GMI, and a recombinant FIP-gja.

2. The method of claim 1, wherein the immunomodulatory protein of Ganoderma or the recombinant thereof has:

an amino acid sequence of (1) LAWNVK; (SEQ ID NO: 1)

(2) DLGVRPSYAV; (SEQ ID NO: 2)

(3) an amino acid sequence of (SEQ ID NO: 3)
MSDTALIFTLAWNVKQLAFDYTPNWGRGRPSSFIDTVTFPTVLTDKAYT

YRVVVSGKDLGVRPSYAVESDGSQKINFLEYNSGYGIADTNTIQVYVID

PDTGNNFIVAQWN;

-continued or an amino acid sequence of
(SEQ ID NO: 4)
EAEAEFMSDTALIFTLAWNVKQLAFDYTPNWGRGRPSSFIDTVTFPTVL

TDKAYTYRVVVSGKDLGVRPSYAVESDGSQKINFLEYNSGYGIADTNTI

QVYVIDPDTGNNFIVAQWNYLEQKLISEEDLNSAVDHHHHHH.

3. The method of claim 1, wherein the immunomodulatory protein of *Ganoderma* or the recombinant thereof contacts a human epithelial cell and a B cell in the subject.

4. The method of claim 3, wherein binding of a virus that causes the viral infection onto the human epithelial cell and the B cell is inhibited by the immunomodulatory protein of *Ganoderma* or the recombinant thereof contacting the human epithelial cell and the B cell.

5. The method of claim 1, wherein the *Ganoderma* is *Ganoderma lucidum, Ganoderma tsugae, Ganoderma microsporum* or *Ganoderma sinensis*.

6. The method of claim 1, wherein a virus that causes the viral infection is selected from the group consisting of herpes simplex viruses 1 and 2, varicella zoster virus, Epstein-Barr virus (EBV), human cytomegalovirus (HCMV), herpesvirus 6, 7, and Kaposi Sarcoma-associated virus (KSHV).

7. The method of claim 6, wherein the virus is Epstein-Barr virus (EBV).

8. The method of claim 1, wherein the administering of the immunomodulatory protein of *Ganoderma* or a recombinant thereof decreases an infectivity of a virus that causes the viral infection.

\* \* \* \* \*

SEQUENCE LISTING

```
Sequence total quantity: 4
SEQ ID NO: 1            moltype = AA   length = 6
FEATURE                 Location/Qualifiers
source                  1..6
                        mol_type = protein
                        organism = Ganoderma microsporum
SEQUENCE: 1
LAWNVK                                                                      6

SEQ ID NO: 2            moltype = AA   length = 10
FEATURE                 Location/Qualifiers
source                  1..10
                        mol_type = protein
                        organism = Ganoderma microsporum
SEQUENCE: 2
DLGVRPSYAV                                                                 10

SEQ ID NO: 3            moltype = AA   length = 111
FEATURE                 Location/Qualifiers
source                  1..111
                        mol_type = protein
                        organism = Ganoderma microsporum
SEQUENCE: 3
MSDTALIFTL AWNVKQLAFD YTPNWGRGRP SSFIDTVTFP TVLTDKAYTY RVVVSGKDLG           60
VRPSYAVESD GSQKINFLEY NSGYGIADTN TIQVYVIDPD TGNNFIVAQW N                   111

SEQ ID NO: 4            moltype = AA   length = 140
FEATURE                 Location/Qualifiers
source                  1..140
                        mol_type = protein
                        organism = synthetic construct
SEQUENCE: 4
EAEAEFMSDT ALIFTLAWNV KQLAFDYTPN WGRGRPSSFI DTVTFPTVLT DKAYTYRVVV           60
SGKDLGVRPS YAVESDGSQK INFLEYNSGY GIADTNTIQV YVIDPDTGNN FIVAQWNYLE          120
QKLISEEDLN SAVDHHHHHH                                                     140
```